(12) United States Patent
Boese et al.

(10) Patent No.: US 7,596,406 B2
(45) Date of Patent: Sep. 29, 2009

(54) DEVICE FOR RECORDING ELECTROPHYSIOLOGICAL SIGNALS AND FOR DISPLAYING THE SIGNALS OR SIGNAL INFORMATION ELEMENTS WHICH ARE DERIVED THEREFROM

(75) Inventors: Jan Boese, Eckental (DE); Martin Kleen, Furth (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 694 days.

(21) Appl. No.: 11/347,549

(22) Filed: Feb. 3, 2006

(65) Prior Publication Data

US 2006/0241518 A1  Oct. 26, 2006

(30) Foreign Application Priority Data

Feb. 3, 2005 (DE) ......................... 10 2005 005 037

(51) Int. Cl.
*A61B 5/44* (2006.01)
(52) U.S. Cl. ...................................... 600/523; 600/525
(58) Field of Classification Search ................. 600/373, 600/509, 523, 466, 465, 525
See application file for complete search history.

(56) References Cited

U.S. PATENT DOCUMENTS

| 5,662,108 A * | 9/1997 | Budd et al. ................. 600/374 |
| 6,264,653 B1 * | 7/2001 | Falwell ......................... 606/41 |
| 6,456,864 B1 * | 9/2002 | Swanson et al. ............ 600/374 |
| 6,615,072 B1 | 9/2003 | Izatt et al. |
| 2004/0254437 A1 | 12/2004 | Hauck et al. |

FOREIGN PATENT DOCUMENTS

WO  WO 2004/103174 A1  12/2004

* cited by examiner

*Primary Examiner*—Carl H Layno
*Assistant Examiner*—Natasha Patel (57) ABSTRACT

Device for recording electrophysiological signals and for displaying the signals or signal information elements which are derived therefrom, comprising a catheter which includes a plurality of electrodes arranged in a distributed manner for signal recording and a rendition device for displaying the signals or the individual signal information elements which relate to the respective electrodes and are derived from the signals, wherein the signals or the signal information elements can be displayed in a display which is modeled on the geometric arrangement of the electrodes at the catheter or on the geometric arrangement of the electrodes during the signal recording.

14 Claims, 5 Drawing Sheets

DEVICE FOR RECORDING ELECTROPHYSIOLOGICAL SIGNALS AND FOR DISPLAYING THE SIGNALS OR SIGNAL INFORMATION ELEMENTS WHICH ARE DERIVED THEREFROM

CROSS REFERENCE TO RELATED APPLICATIONS

This application claims priority to the German Application No. 10 2005 005 037.9, filed Feb. 3, 2005 which is incorporated by reference herein in its entirety.

FIELD OF INVENTION

The invention relates to a device for recording electrophysiological signals and for displaying the signals or a signal information element which is derived therefrom, comprising a catheter which includes a plurality of electrodes arranged in a distributed manner for signal recording and a rendition device for displaying the signals or the individual signal information elements which relate to the respective electrodes and are derived from the signals.

BACKGROUND OF INVENTION

Detection and recording systems for electrophysiological signals such as standard ECG derivatives or intracardial ECG derivatives record electrophysiological signals and display the signals one above the other in a vertical series on a monitor. The reason for this vertical display of signals one above the other on the monitor is because the display is modeled on the output of a mechanical ECG plotter which was used previously. In the context of electrophysiological procedures, catheters are inserted inter alia into cavities or vessels such as the heart chambers, for example, coronary sinuses or the pulmonary vein openings, wherein such catheters have a plurality of electrodes for intercardial ECG derivation, said electrodes being arranged in a distributed manner. In this case, the electrodes are positioned differently in accordance with the design of the catheter. In the case of a lasso catheter the electrodes are arranged annularly in a distributed manner at a terminating catheter section, for example, whereas in the case of a coronary sinus catheter they are arranged along the catheter, for example. Such a lasso catheter can be introduced into the pulmonary vein opening in the left-hand atrium, for example, wherein the front catheter ring lies against the vessel wall in a manner which corresponds to its cross section, i.e. it is therefore positioned there in a manner which is likewise annular or possibly somewhat oval. A coronary sinus catheter is introduced into e.g. the corresponding sinus curve which connects the two atria. This catheter is elongated by nature, the electrodes being longitudinally distributed and preferably spaced at equal intervals. In the recording position, i.e. when the catheter is positioned in the sinus curve, the catheter adapts itself to the form of the curve however, in other words the electrodes likewise extend along an arced line.

SUMMARY OF INVENTION

It is therefore clear that the spatial relation of the electrodes can be indiscriminate, particularly when they are introduced into the examination object. The usual display of signals in the form of a vertical series nonetheless takes place in each case using previously known recording systems. Consequently, it is laborious for the doctor to allocate the individual signals to corresponding electrodes. Although the doctor receives the usual information via the signal or the signal information element itself, a spatial assignment has not been possible until now.

The invention therefore addresses the problem of specifying a device which allows an improved display of signals or signal information elements.

In order to solve this problem, in the case of a device of the type described at the beginning, the invention provides for allowing the signals or signal information elements to be displayed in a display which is modeled on the geometric arrangement of the electrodes at the catheter or on the geometric arrangement of the electrodes during the signal recording, in order to allow a spatial assignment of the signals or the signal information element to the relevant electrodes.

Unlike all previously known display forms, the claimed device offers the possibility of allowing the signal display or signal information element display of the spatial relation of the electrodes to each other according to their original positioning at the catheter itself or according to the actual form assumed by the catheter when it is introduced into the vessel or organ. The signals or signal information elements are therefore represented in a geometric arrangement which is approximately the geometric arrangement of the electrodes at the catheter when it has not been introduced, or the geometric arrangement of the electrodes at the catheter when it has been introduced and the signals are being recorded. Therefore the channel layout of the signals or signal information element display essentially follows the actual electrode geometry and is not chosen in a completely abstract manner as in the case of previously usual displays.

This results in a simpler, more intuitive understanding of the display for the doctor, since he or she also receives information about the spatial assignment of the signals themselves.

In this case, a first alternative of the invention provides for rendering the signals or the signal information elements in a midpoint-oriented radial display which corresponds to the electrode arrangement and has a shared center, when using an essentially annular arrangement of the electrodes at the catheter. An example of such a catheter is the lasso catheter already cited at the beginning. The display form which is modeled on its original annular form consequently allows an easy allocation of the signals or signal information elements. In this case, such an essentially annular midpoint-oriented display is obviously also understood to include a somewhat oval display, if it is assumed that the catheter is compressed in a somewhat oval manner in the recording position. As described in greater detail below, the actual form of the introduced catheter can be detected using a corresponding position detection system and taken as a basis for the selected display form. Alternatively, of course, it is also possible to derive the actual catheter form from the fluoroscopy display which is often carried out in parallel.

The signals can be displayed alone in this case, wherein the display takes place in a radial star-shaped arrangement. The continuously recorded signals are therefore output immediately—as in the case of conventional displays—but in a completely different display which is modeled on the annular form in a star-shaped arrangement relative to each other, i.e. they extend towards a midpoint or outwards from this midpoint to the side. In practical terms, one signal is displayed on each "beam", wherein the number of "beams" corresponds to the number of electrodes.

According to the invention, the amplitude of the signals can increase from the center outwards, in order to prevent those individual signals which intersect there from overlapping excessively or at all towards the midpoint. Equally, it is possible to update the signals in the manner of a "windscreen wiper", i.e. the recordings and therefore also the displays and the overwriting of all signals begins afresh as soon as a signal has run to the outer or inner limit of the displayed structure. Alternatively, the recording and therefore also the overwriting can be started afresh as soon as a specific defined time point of the heart cycle is reached ("windscreen-wiper mode in the heart rhythm"). Therefore all known and possible signal rendition forms can also be used in the context of the claimed display possibility.

An alternative to the quasi star-shaped display including signals which preferably run outwards provides for the display area to be divided into a plurality of area segments corresponding to the number of electrodes, said area segments comprising the same number of radially arranged arc segments in each case, wherein the signal of the assigned electrode, a part of the signal, or a signal information element which is derived from the continuously recorded signal of the electrode can be displayed in each arc segment. In this alternative of the invention, the display area is divided into a plurality of "cake segments" which are in turn divided again into radially arranged arc segments. The corresponding signal or signal information element display now takes place within each individual arc segment. A signal assignment which is intuitively better can also take place in the case of such a display. In this case, each arc segment is assigned a specific time window, in which a specific section of the signal is placed. However, it is also conceivable to assign one or more defined heart cycles to each arc segment, and to display the corresponding signals or signal information elements, which are received from the assigned cycles, in the relevant arc segment. The outer segments of the relevant area segment, this having the form of a "cake slice", preferably represent the currently derived signal, while the segments lying further inwards represent the past time segments or cycles. The time-relative component is therefore rendered by the location of the segments on the segmented structure.

In this case, it is possible on one hand to assign a complete area segment to an electrode, so that the same number of area segments is provided as there are electrodes at the catheter.

Alternatively, however, it is also conceivable within an area segment to assign an arc segment to a different electrode in each case, wherein the assignment is selected in such a way that the arc segments of the various area segments, said arc segments being assigned to an electrode, describe a spiral. This means that the electrode-related segment display moves quasi around the center from area segment to area segment, preferably from the outside inwards, wherein the outer segment of the circle once again shows the signal which is currently derived, while segments lying further inwards represent past time segments.

The linear electrode arrangement must be cited as an alternative to the annular electrode structure. In such a case, the signal display or signal information element display also takes place as a display which corresponds to the geometric electrode arrangement in the recording position of the catheter. To a large extent, such a catheter adapts its form to the form of the vessel, and therefore it can assume any geometric form during the recording. A more or less linear or arced form is primarily assumed, as is the case when a catheter is placed in the coronary sinus, for example. Once again, the signal display or information element display corresponds to the actual arrangement of the electrodes relative to each other, i.e. depending on the actual catheter form in the vicinity of the electrodes.

In this case, the display can be divided into a plurality of fields corresponding to the number of electrodes, wherein the signals can be displayed alone in this case. Therefore, instead of the star-shaped display cited for the first embodiment, provision is made here for an area display of the circular segment or annular segment type, featuring a number of fields that corresponds to the number of electrodes, wherein the continuously recorded signals are directly displayed in each field, said signals again in this case being overwritable in the manner of a "windscreen wiper".

Alternatively, there is the possibility of dividing the display into a plurality of fields corresponding to the number of electrodes, said fields comprising the same number of field segments in each case, wherein the signal of the assigned electrode, a part of the signal, or a signal information element which is derived from the continuously recorded signal of the electrode can be displayed in each field segment. This embodiment corresponds to the previously described display form featuring the area segments in the form of "cake segments". However, each field is preferably assigned to an electrode in this embodiment, though "travel" of the individual time-relative signal components from field to field and therefore from field segment to field segment is nonetheless likewise conceivable.

In a particularly advantageous development of the invention, the signal information element can be displayed in the form of a color-coded image display in an arc segment. In the segmented display means, the relevant signal information element is therefore rendered in a color-coded manner, wherein the color-coding can be determined e.g. with reference to the average amplitude of the currently recorded signal, or time-relative signal portion, which is assigned to an arc segment or a field segment.

When using the color-coded display with the "cake segment display", e.g. using all information elements displayed in the outer arc segment, said information elements always showing the information element which is currently being recorded (irrespective whether an area segment is assigned to just one electrode, or whether the individual arc segments are assigned to the different electrodes), the doctor can understand the time-relative signal sequence of all current electrode signals with reference to the color coding in each case. If an area segment is assigned to a single electrode, the doctor can easily read the time-relative sequence of the electrode signal by directly comparing the color coding of the individual arc segments.

Furthermore, it is appropriate at the catheter to provide one or more elements for detecting the catheter position by means of a position detection system such that, knowing the catheter position within the display, the signal or signal information element which is shown in each case can be assigned to a specific electrode. As a result of this position detection, it is known which electrode is now positioned exactly at which location in the vessel, i.e. the first electrode and all further n electrodes can be localized exactly. The display of the individual electrode signals—particularly in the case of a star-shaped or arc-segment display type—can be configured in such a way that the signals originating from the first electrode are displayed at a position which corresponds essentially to the actual electrode position in the vessel, seen in relation to the wall of the vessel.

Furthermore, it is particularly advantageous at the catheter to provide one or more elements for detecting the physical location of the catheter by means of a position detection system, wherein the form of the display can be selected depending on the physical location of the catheter. As briefly described above, in this configuration of the invention the actual two-dimensional or three-dimensional location of the catheter is detected such that its exact form is determined, i.e. whether it is actually annularly positioned or compressed, whether its arrangement is predominantly linear, i.e. extended, or more or less markedly arced, and the actual display form can be selected according to the actual catheter form and therefore according to the actual arrangement of the electrodes.

BRIEF DESCRIPTION OF THE DRAWINGS

Further advantages, features and details of the invention are derived from the exemplary embodiments described below and with reference to the drawings, in which.

DETAILED DESCRIPTION OF INVENTION

Figure 1:
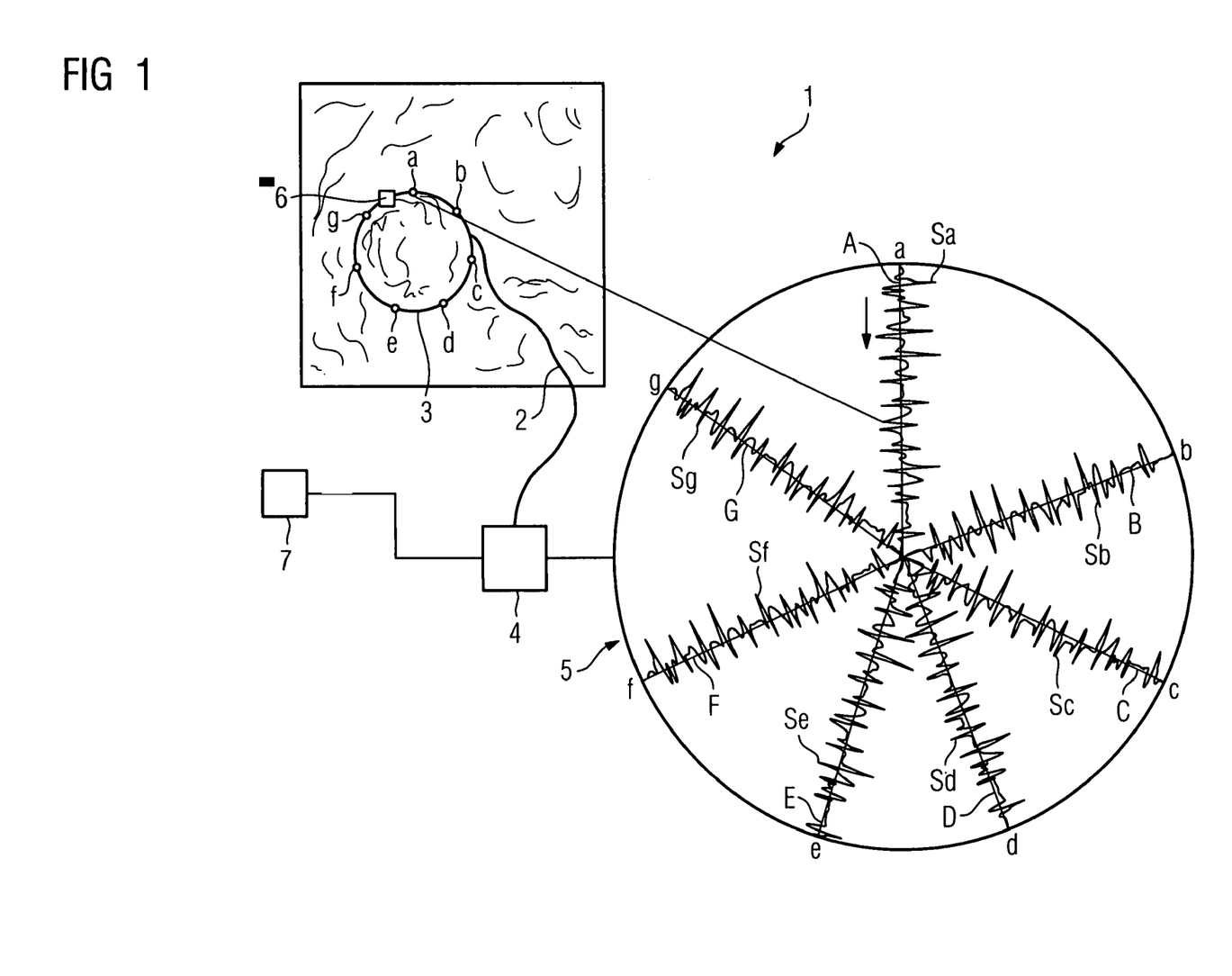
FIG. 1 shows a schematic representation of a claimed device in a first embodiment having a star-shaped signal display.

In the form of a schematic representation, FIG. 1 shows a claimed device 1 comprising a fluoroscopically detected catheter 2 which has been introduced into the pulmonary vein in the example, said catheter having the form of a lasso catheter and having seven electrodes a, b, c, d, e, f and g which are distributed at a terminating annular structure 3 in the example which is shown. The electrodes are all provided for separate signal recording and communicate via signal lines, which are not shown in further detail, with a signal processing device 4 to which a rendition device 5 in the form of a monitor is assigned, wherein only the signal display area is shown by the monitor.

FIG. 1 clearly shows that the display of the individual signals of the electrodes a-g corresponds to the distribution of the electrodes. The electrodes are annularly arranged as shown in FIG. 1, and the individual signal display takes place in a star-shaped manner, wherein each beam A, B, C, D, E, F and G is assigned to an electrode. The signal Sa of the electrode a is displayed on the beam A, the signal Sb of the electrode b is correspondingly rendered on the beam B, etc. The signals preferably travel in the manner which is illustrated by the arrow at beam A, from the outside inwards to the center of the display. The signals are recorded continuously as in the case of conventional displays and they can be overwritten, etc. and therefore all usual signal display possibilities are also conceivable here.

In order to allow an assignment of the relevant beam to the relevant electrode and also actually—in the example which is shown—to display the signal of the electrode a at the top position, thereby corresponding to the actual physical location of the electrode, provision is made on the annular structure 3 for an element 6 which can be detected by a position detection system 7, said position detection system being shown only schematically. Since the image display is concerned with a two dimensional display, it is sufficient to determine the two-dimensional location of the element, since only the relative location of the electrodes in the space will be determined from this. The position detection system 7 communicates with the image processing device 4, which then selects and "turns" the display accordingly in such a way that the signal of the electrode a can actually be rendered at the corresponding upper position, and the other signals can be correctly rendered relative to said electrode a accordingly.

Whereas the signals in FIG. 1 are shown with their actual amplitudes running to the center, it is conceivable to reduce the amplitudes somewhat towards the center, such that the overlapping in the central area is not too pronounced.

Figure 2:
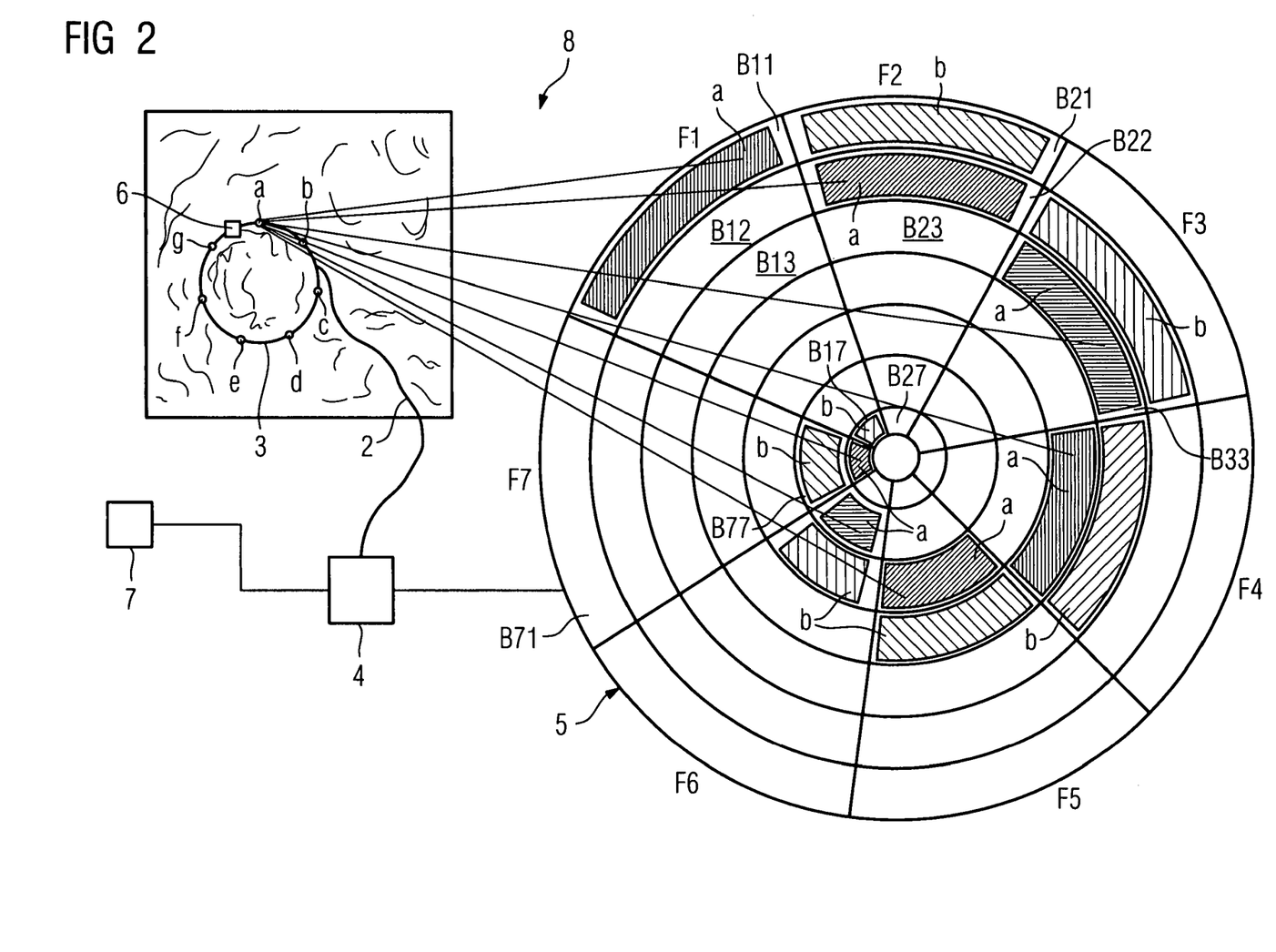
FIG. 2 shows a schematic representation of a claimed device in a second embodiment having a cake-segment display in a first display form.

FIG. 2 shows a claimed device 8 which likewise comprises a catheter 2 including the electrodes a-g arranged on the annular structure 3. Provision is also made here for the image processing device 4 to which a rendition device 5 in the form of a monitor is assigned, and provision is also made here on the annular structure for an element 6 which can be detected via a position detection system 7.

Unlike the device as per FIG. 1, however, there is no display of the individual actual signals here, but a derived color-coded display. The display area is divided into a number of area segments F1, F2, F3, F4, F5, F6 and F7 corresponding to the number of electrodes, said area segments being designed in the manner of cake segments and divided in each case into a multiplicity of arc segments, there being seven such arc segments in the example shown. The arc segments are characterized as follows in the figure:

The area segment F1 has seven arc segments B11, B12, B13, . . . , B17. The area segment F2 has seven arc segments B21, B22, B23, . . . , B27. The same manner of designation continues until the area segment F7 which has seven area segments B71, . . . , B77.

Each area segment is assigned to a specific signal interval, such that a time-oriented assignment takes place. Alternatively, it is also conceivable to assign each arc segment to a specific number of cycles of the rhythmic ECG.

In contrast to the actual signal display, a color-coded signal display takes place as described in this case. A signal information element is determined from the assigned signal portion in each case, e.g. by averaging the amplitudes, and this signal information element is rendered in a color-coded manner. In the example shown, the color codings are displayed by the corresponding image displays in the few highlighted arc segments, said image displays being variously crosshatched. In this case, the display takes place in such a way that the signal information elements which are assigned to an electrode run around in the form of a spiral.

As shown in FIG. 2, a first time-oriented signal information element of the electrode a is displayed in the arc segment B11. The preceding and chronologically earlier signal information element is displayed in the arc segment B22 of the area segment F2. The again chronologically earlier proportional signal information element of the electrode a is then displayed in the arc segment B33 of the area segment F3, etc. The last and chronologically oldest signal information element of the electrode a is then shown in the arc segment B77 of the area segment F7. Correspondingly, the individual flat and color-coded signal information elements of the electrode b run around in the form of a spiral, starting with the chronologically earliest proportional signal information element which is displayed in the arc segment B21 in the area segment F2 and ending with the chronologically oldest proportional signal information element which is displayed in the arc segment B17 in the area segment F1. The display for all other electrodes continues in a corresponding manner.

On the basis of this signal portion display which goes round in a quasi spiral manner, in addition to the previously mentioned spatial relation to the form of the annular lasso catheter, the doctor can also directly compare the time-relative corresponding signals by means of their color coding, said signals in this case being all signals in the outer ring and representing the relevant most chronologically recent signals of the individual electrodes a-g.

Figure 3:
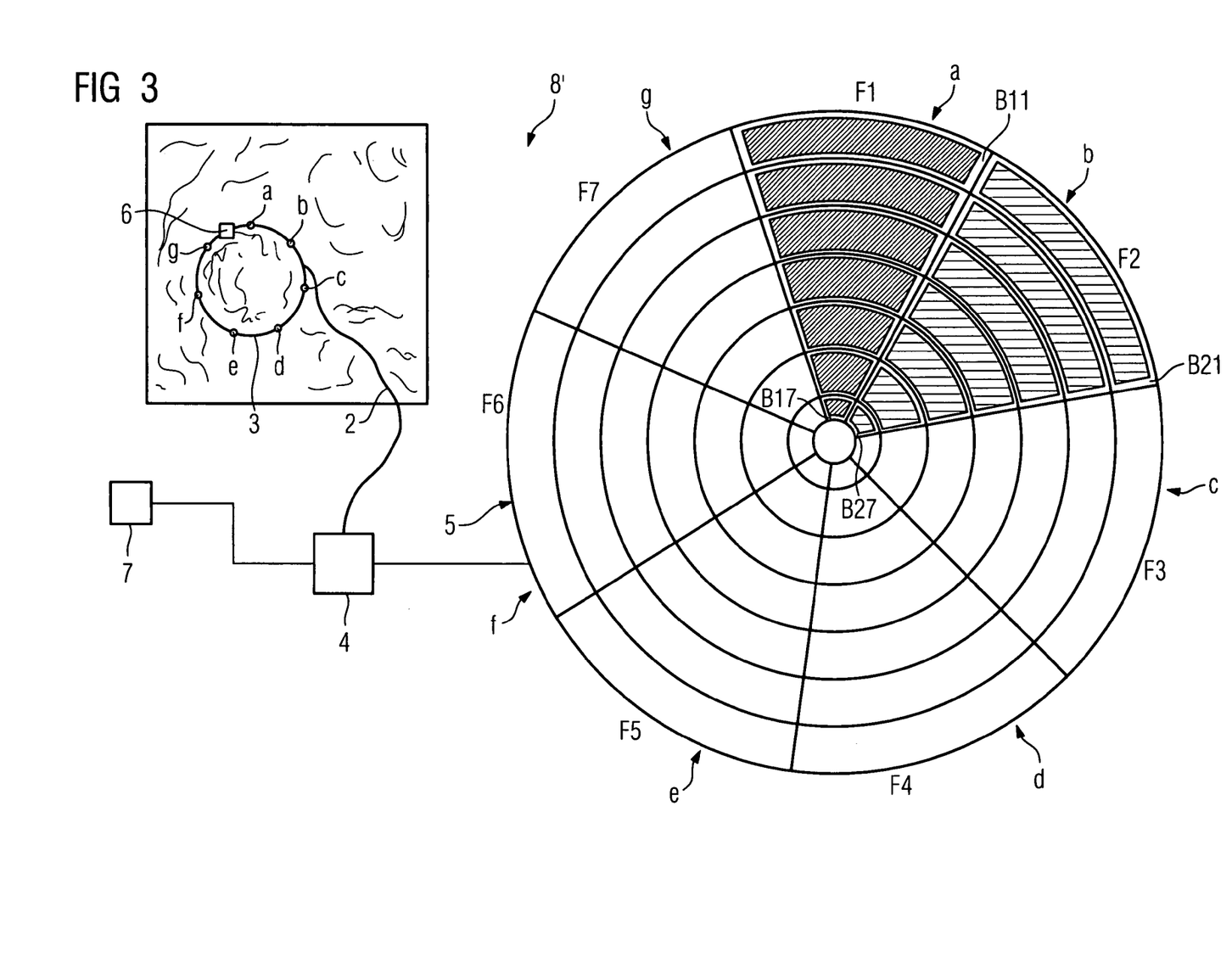
FIG. 3 shows a claimed device in a third embodiment having a cake-segment display in a second embodiment.

A further display variant is illustrated by the claimed device 8' in FIG. 3. The catheter and other elements correspond entirely to the device 8 from FIG. 2, but the display at the rendition device 5 is different. Although a division into seven area segments F1-F7 also takes place here, each area segment is however assigned to an electro de in this case. In the example shown, the area segment F1 is assigned to the electrode a, the area segment F2 to the electrode b, etc. The chronologically consecutive signal information elements of exclusively one assigned electrode are therefore rendered in the individual arc segments B11-B17, B21-B27, etc., wherein the most recent signal information element in each case is displayed again here in the outermost arc segment. The advantage of this display is that the time-relative sequence of a recorded signal of an electrode is rendered by the individual area segments from the outside inwards.

A positionally accurate display is also provided in this case, as in the embodiment according to FIG. 2, in which display the location of the catheter is detected via the element 6 and the position detection system, such that precisely the signals or signal information elements of the electrode a can actually be rendered in the upper display area and the other signal information elements of the adjacent electrodes can be correctly positioned correspondingly.

Figure 4:
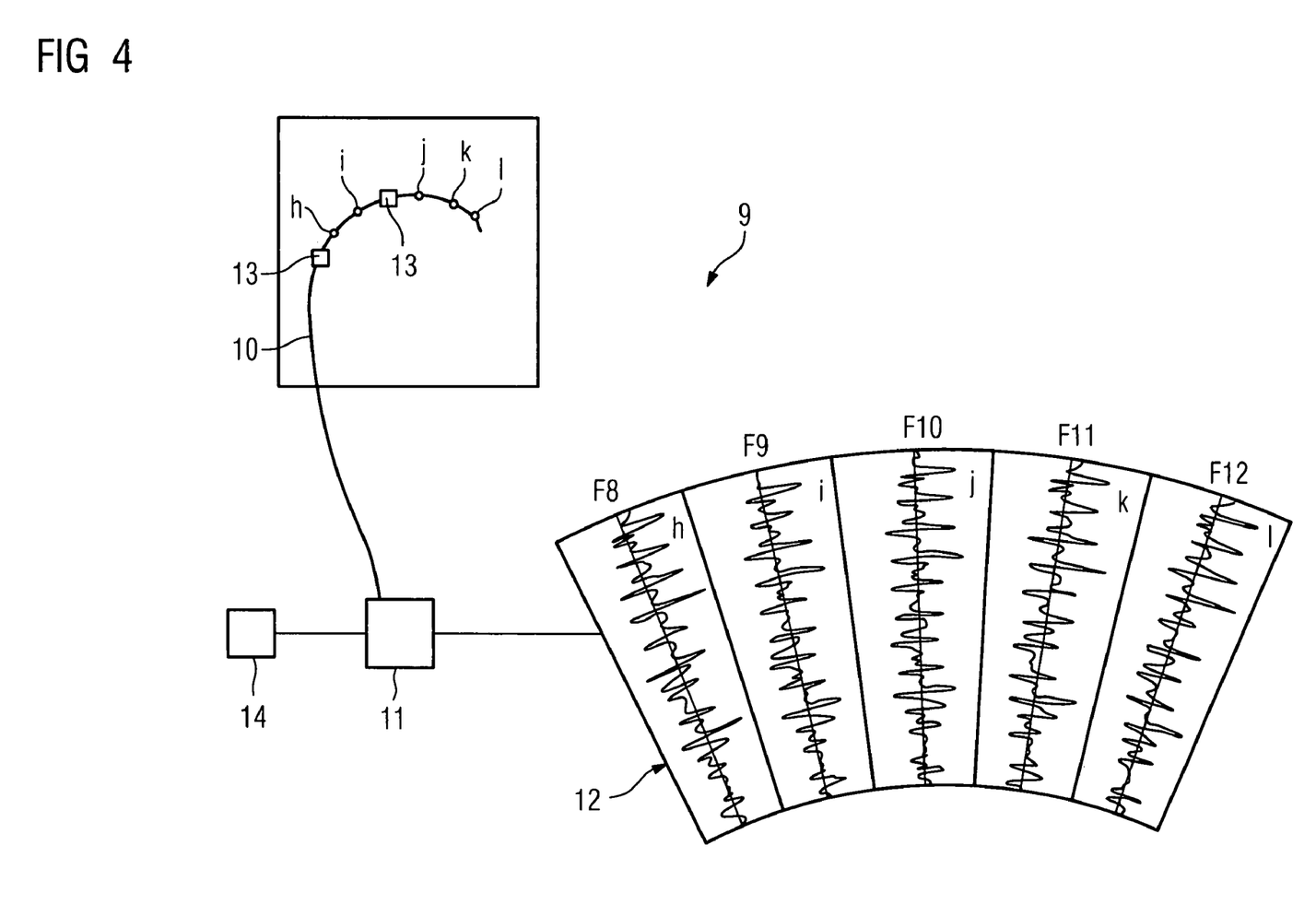
FIG. 4 shows a claimed device in a fourth embodiment having linearly arranged electrodes and a signal display.

FIG. 4 shows a further embodiment of a device 9 according to the invention, comprising a fluoroscopically detected catheter 10 which has been introduced into the coronary sinus in this case, wherein a plurality of longitudinally distributed electrodes h, i, j, k, l are arranged at said catheter. The catheter 10 is connected to an image processing device 11 which in turn outputs the corresponding signals at a rendition device 12. Provision is made for two elements 13 at the catheter 10 in this example, said elements being detected via the position detection system 14 in order to determine the spatial location of the catheter therefrom.

The form of the display is selected at the recording instant depending on the detected spatial location, which is arced in this case because the catheter is inserted e.g. into the coronary sinus curve. As shown in the figure, the signal display also has the form of an arc. The display area 14 is divided into a plurality fields F8, F9, F10, F11, F12, producing a display having the form of an annular section. The signal of one of the electrodes h-l is assigned to each of the fields F8-F12. For example, the signal of the electrode h is displayed in the field F8, the signal of the electrode i in the field F9, etc., and the signal of the electrode l is displayed in the field F12. A precise signal assignment is possible from the detection of the position via the position detection system.

Since it is known how the electrodes lie relative to the examination area, the doctor can use the claimed display to assign exactly which electrode lies where and which signal it records.

Figure 5:
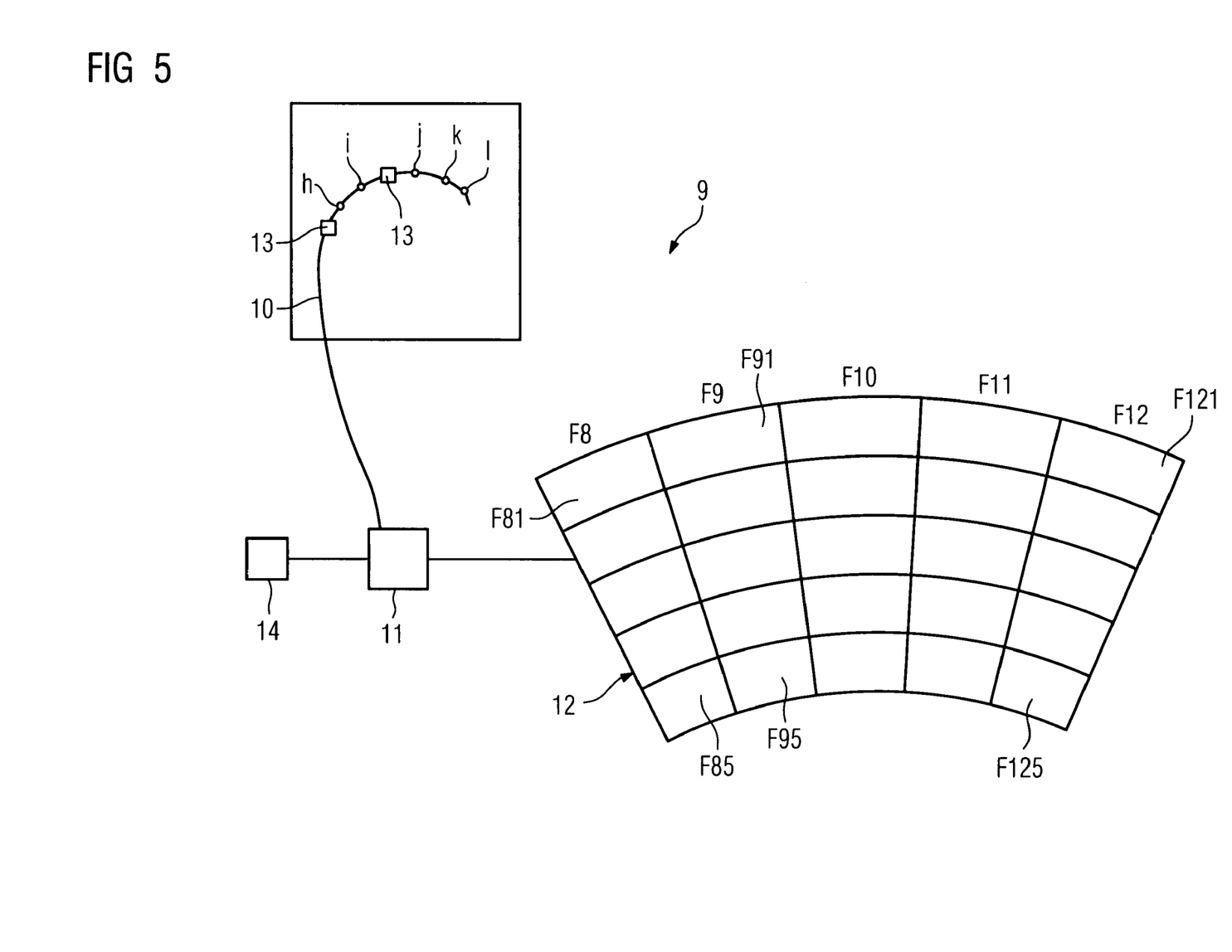
FIG. 5 shows a claimed device in a fifth embodiment having linearly arranged electrodes and a segment display.

FIG. 5 shows a display which corresponds to the device from FIG. 3. The fields F8-F12 are provided again and the display area is divided into these. In addition to this, however, each field is divided into a plurality of field segments called F81, F82, . . . , F85, F91, . . . , F95, through to the field F12 with the field segments F121, . . . , F125. A display which corresponds to the color-coded displays of the signal information element from the FIGS. 2 and 3 is produced again here. Therefore the corresponding chronologically consecutive signal information elements of the signals of the electrode h, e.g. with reference to the average amplitude, are displayed in the field segments F81-F85 of the field F8, such that a chronologically color-coded signal sequence corresponding to the display from FIG. 3 can be recognized. The same applies correspondingly in relation to the electrodes i-l which are displayed in the fields F9-F12 and their area segments.

As described, the position detection system 14 in connection with the element(s) 13 allows the detection of the actual catheter form in the vicinity of the electrodes, and therefore the exact geometry of the catheter area and therefore also the exact position of the electrodes relative to each other can be determined. The display form is now selected by the image processing device 11 such that it corresponds to the catheter form or electrode arrangement. If the catheter section including the electrodes were more markedly curved, for example, the annular section of the display area would also be more markedly curved accordingly, and vice versa. Even more complex structures, in which a catheter section is e.g. coiled several times, can be reproduced precisely in this way.

The invention claimed is:

1. A device for recording and displaying electrophysiological signals or signal information elements derived from electrophysiological signals, the device comprising:
 a catheter including a plurality of electrodes for acquiring electrophysiological signals, the plurality of electrodes having a distributed geometric arrangement on the catheter; and
 a display device for displaying the electrophysiological signals or the signal information elements,
  wherein the display device is configured to display the respective electrophysiological signals or the signal information elements in a display arrangement corresponding to the distributed geometric arrangement of the electrodes or corresponding to a current spatial geometric arrangement of the electrodes relative to a three-dimensional environment while acquiring the electrophysiological signals,
  wherein
   the electrophysiological signals are time domain signals acquired and displayed continuously in a time display where each of the plurality of electrodes has a corresponding time domain signal and all of the corresponding time domain signals are displayed simultaneously, and
   the signal information elements are determined by averaging an amplitude of a respective electrophysiological signal associated with a respective electrode, and where the signal information element is rendered in a color-coded manner and all of the corresponding signal information elements are displayed simultaneously and arranged in cake segments.

2. The device as claimed in claim 1, wherein
 the distributed geometric arrangement is an essentially annular arrangement, and
 the electrophysiological signals respectively the signal information elements are displayed in a midpoint-oriented radial display corresponding to the annular arrangement, the midpoint-oriented radial display having a common center point relative to which the electrophysiological signals or the signal information elements are displayed.

3. The device as claimed in claim 2, wherein the electrophysiological signals are displayed in a radial star-shaped arrangement.

4. The device as claimed in claim 3, wherein the star-shaped arrangement includes an amplitude of the electrophysiological signals, the amplitude increasing in an outward radial direction relative to the center point.

5. The device as claimed in claim 3, wherein the electrophysiological signals are acquired and displayed continuously in a time display and extending in an outward radial direction relative to the center point or in an inward radial direction relative to the center point, the radial direction corresponding to a time axis.

6. The device as claimed in claim 2, wherein a complete display segment is assigned to each electrode.

7. The device as claimed in claim 6, wherein each arc segment is assigned to a different electrode within one display segment, and
all arc segments assigned to the same electrode are displayed in the form of a spiral.

8. The device as claimed in claim 1, wherein
the distributed geometric arrangement is an essentially linear arrangement, and
the electrophysiological signals respectively the signal information elements are displayed in a display arrangement corresponding to a geometric electrode arrangement relative to a recording position of the catheter.

9. The device according to claim 8, wherein the display arrangement includes an arced form shaped as annular sections.

10. The device as claimed in claim 9, wherein
the display arrangement includes a plurality of fields corresponding to the number of electrodes, and
each electrophysiological signal is displayed in one field.

11. The device as claimed in claim 9, wherein
the electrophysiological signals are acquired continuously,
the display arrangement is divided into a plurality of fields corresponding to the number of electrodes, each field comprising the same number of field segments, and
each electrophysiological signal, a part of the electrophysiological signal, or a signal information element derived from the electrophysiological signal is displayed in one field segment.

12. The device as claimed in claim 2, wherein the color-coded cake segment is an arc segment.

13. The device as claimed in claim 1, further comprising a position locating device assigned to the catheter for determining a current catheter position such that each electrode and its corresponding electrophysiological signal can be identified in the display of the electrophysiological signals based on the catheter position.

14. The device as claimed in claim 13, wherein
the position locating device is configured to determine a current three-dimensional catheter position, and
the electrophysiological signals respectively the signal information elements are displayed relative to the current three-dimensional catheter position.

* * * * *